United States Patent
Myers et al.

(10) Patent No.: US 7,464,021 B1
(45) Date of Patent: Dec. 9, 2008

(54) COMPUTER SYSTEM FOR TRANSLATING MEDICAL TEST RESULTS INTO PLAIN LANGUAGE

(75) Inventors: Wayne R. Myers, Smithville, MO (US); Angela K. Rouse, Kansas City, MO (US); Tommy L. Hinton, Leawood, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 944 days.

(21) Appl. No.: 09/829,273

(22) Filed: Apr. 9, 2001

Related U.S. Application Data (60) Provisional application No. 60/266,411, filed on Feb. 2, 2001.

(51) Int. Cl.
*G06F 17/28* (2006.01)
*G09B 23/28* (2006.01)

(52) U.S. Cl. .............. 704/7; 128/920; 706/45
(58) Field of Classification Search .......... 704/9, 704/7, 3, 45, 10, 8, 232; 705/3; 706/45; 128/920
See application file for complete search history.

(56) References Cited

U.S. PATENT DOCUMENTS

| | | | |
|---|---|---|---|
| 5,437,278 A * | 8/1995 | Wilk | 600/425 |
| 5,551,436 A * | 9/1996 | Yago | 600/483 |
| 5,746,204 A * | 5/1998 | Schauss | 600/300 |
| 5,754,111 A | 5/1998 | Garcia | |
| 5,823,948 A * | 10/1998 | Ross et al. | 600/300 |
| 5,839,438 A * | 11/1998 | Graettinger et al. | 600/300 |
| 5,878,746 A * | 3/1999 | Lemelson et al. | 600/407 |
| 6,018,713 A * | 1/2000 | Coli et al. | 705/2 |
| 6,049,794 A * | 4/2000 | Jacobs et al. | 706/45 |
| 6,270,456 B1 * | 8/2001 | Iliff | 600/300 |
| 6,312,378 B1 * | 11/2001 | Bardy | 600/300 |
| 6,336,900 B1 * | 1/2002 | Alleckson et al. | 600/485 |
| 6,377,162 B1 * | 4/2002 | Delestienne et al. | 340/286.07 |
| 6,455,321 B1 * | 9/2002 | Chace | 436/173 |
| 6,629,937 B2 * | 10/2003 | Watrous | 600/586 |
| 7,099,801 B1 * | 8/2006 | McBride et al. | 702/188 |
| 2003/0208108 A1 * | 11/2003 | Shewmake et al. | 600/300 |

OTHER PUBLICATIONS

Aikins et al. PUFF: An Expert System for Interpretation of Pulmonary Function Data, Sep. 1982, Stanford University, p. 1-21.*
Kim Binsted et al., "Generating Personalised Patient Information Using the Medical Record", Proceedings of the 5th Conference on Artificial Intelligence in Medicine Europe: Artificial Intelligence Medicine, Jun. 1995.*

* cited by examiner

*Primary Examiner*—Talivaldis I Smits
(74) *Attorney, Agent, or Firm*—Shook, Hardy & Bacon L.L.P.

(57) ABSTRACT

A method for translating medical test results into plain language is provided. The method includes receiving a medical test result for a type of medical test and, after making a threshold determination whether the medical test result will initially be automatically interpreted by the computer system independent of clinician input, identifying a template or set of templates associated with the type of medical test. The method also includes selecting the template matching the medical test result and outputting a plain language explanation based on the selected template.

54 Claims, 6 Drawing Sheets

COMPUTER SYSTEM FOR TRANSLATING MEDICAL TEST RESULTS INTO PLAIN LANGUAGE

CROSS-REFERENCE TO RELATED APPLICATIONS

This application claims the benefit of U.S. Provisional Application No. 60/266,411, filed Feb. 2, 2001.

STATEMENT REGARDING FEDERALLY SPONSORED RESEARCH AND DEVELOPMENT

"Not Applicable"

TECHNICAL FIELD

The present invention relates to a computer system and, more particularly, to a computer system for translating medical test results into plain language.

BACKGROUND OF THE INVENTION

Medical tests are critical to the diagnosis and treatment of health conditions. Oftentimes, when a patient visits a physician, a number of tests and procedures are performed. However, the physician is unable to communicate the results of the tests and procedures during the same visit because the results are not available instantaneously. For example, when bodily fluids such as blood are extracted by a member of the physician's office staff, the fluids must be sent to a remote laboratory for analysis. In other cases, x-rays and other test results must be reviewed by specialists that are typically unavailable to review the results immediately. Accordingly, it is common for the patient to call the treating physician at a later date to receive the medical test results.

In the past, it has been difficult for physicians and members of their office staffs to document and respond to the high volume of patient and family calls in an efficient manner. In some offices, more than 200 calls per physician per day are common. Also, the Health Care Financing Administration (HCFA) requires that each phone message receive the same documentation and scrutiny as a scheduled visit to the physician's office. Currently, as each call is received, the staff member receiving the call must verify the patient's name, the treating physician's name, record the time and date of the call and find the paper chart for the patient. Then, a nurse or physician's assistant must review the chart and decide whether the nurse is qualified to answer the question or whether the physician is required to answer the question. If the nurse is not capable of answering the question, the nurse must contact the physician to communicate the question, and provide the chart or other information needed to answer the question. Next, either the physician or nurse calls the patient to answer the question. Finally, the communication from the physician's office to the patient is documented.

There are numerous inefficiencies associated with this process. For example, for the most basic test results, the process involves the efforts of at least three individuals, and the inefficiencies associated with the receipt and communication of information from one person to the next. Moreover, the manual steps of receiving the patient's information and documenting each inquiry involve a great deal of effort on the part of the physician and office staff, and lead to numerous opportunities for human errors and omissions. From the patient's perspective, the process also presents a number of disadvantages. In addition to the time delay, the patient must initiate and receive the response at times dictated by the schedules of the office staff and physician. Additionally, the patient ultimately bears the costs of the administration required to respond to the calls and the time lost for the doctor to respond to the inquiries. Moreover, the patient can only receive the information through a phone call or subsequent visit instead of receiving the information at the time and in the format most convenient for the patient.

It is difficult to automate the process for a number of reasons. For example, the test results are typically in a form only understandable by physicians or other clinicians trained in the medical field. Thus, if the actual results of a test are simply communicated to the patient, the patient is likely to be confused as to the implications of the results, and will oftentimes call the physician to discuss the results. If this occurs, any benefit derived by delivering the results via a non-physician are essentially lost. Also, some results are inappropriate to deliver via an automated system, such as results indicating a critical illness. Similarly, the security of the results must be considered in automating the process.

Accordingly, there is a need for an effective system and method for receiving and responding to inquiries from patients regarding medical care test results. There is also a need for a system and method for documenting the receipt of the patient inquiry, the interpretation of the test results and the delivery of the results. A need also exists for a system and method for delivering medical test results in plain language that is understandable by a patient without medical expertise. Still another need exists for a convenient and secure system and method to exchange information between the patient and physician's office.

BRIEF SUMMARY OF THE INVENTION

Generally described, a method for translating medical test results into plain language is provided. The method includes receiving a medical test result for a type of medical test and identifying a template or set of templates associated with the type of medical test. The method also includes selecting the template matching the medical test result and outputting a plain language explanation based on the selected template.

In a further aspect of the method, the method includes the steps of determining if the medical test results will be interpreted by a clinician, and selection of the appropriate template by the clinician.

In another further aspect of the method, the method includes the steps of receiving patient information and checking the patient information against a list of patients having authorization to receive the medical test results.

In another aspect of this method, the method includes distributing the results to a treating physician for review prior to the step of outputting the plain language explanation.

In another aspect of the invention, a computer system for translating medical test results into plain language is provided. The system includes a receiving component that receives a medical test result and an identifying component that identifies a template or set of templates associated with the medical test. The system further includes a selecting component that selects the template matching the medical test result and an outputting component that outputs a plain language explanation based on the selected template.

In a further aspect of the invention, a computer-readable medium containing instructions for controlling a computer system to translate medical test results into plain language is provided, by receiving a medical test result for a type of medical test, identifying a template or set of templates associated with the medical test, selecting the template matching the medical test result, and outputting a plain language explanation based on the selected template.

Additional advantages and novel features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWING

The present invention is described in detail below with reference to the attached drawing figures, wherein.

DETAILED DESCRIPTION OF THE INVENTION

Figure 1:
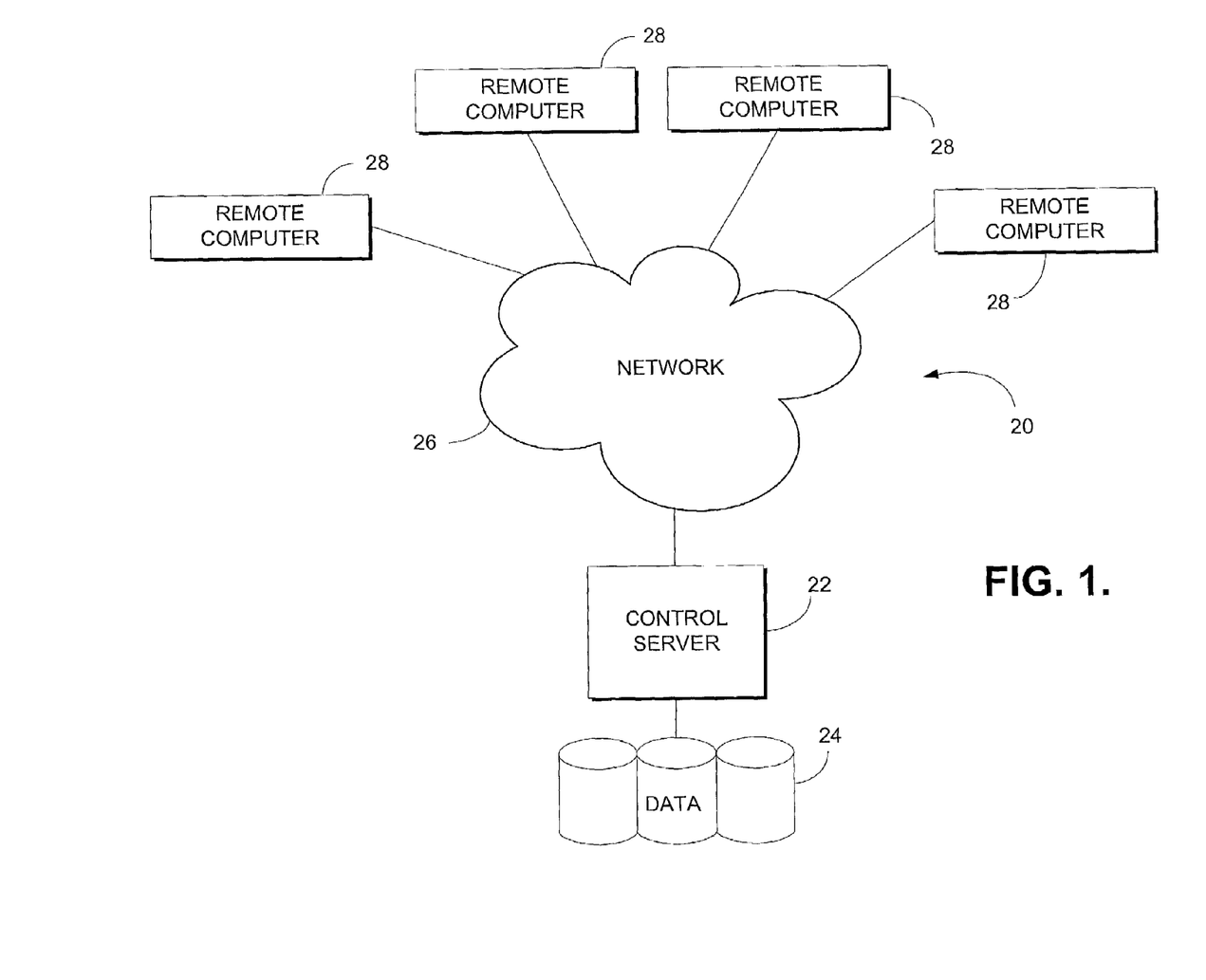
FIG. 1 is a schematic diagram of a suitable computing system environment for use in implementing the present invention.

The present invention provides a method and system for translating medical test results to plain language. FIG. 1 illustrates an example of a suitable medical information computing system environment 20 on which the invention may be implemented. The medical information computing system environment 20 is only one example of a suitable computing environment and is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide a storage of computer readable instructions, data structures, program modules, and other data for server 22.

Server 22 may operate in a computer network 26 using logical connections to one or more remote computers 28. Remote computers 28 can be located at a variety of locations in a medical environment, for example, but not limited to, a clinician's office, testing labs, medical billing and financial offices, hospital administration, and a patient's home environment. Clinicians include, but are not limited to, the treating physician, specialists such as surgeons, radiologists and cardiologists, emergency medical technicians, physician's assistants, nurse practitioners, nurses, nurse's aides, pharmacists, microbiologists, and the like. The remote computers may also be physically located in non-traditional medical care environments such as schools, offices of non-physicians such as speech pathologists, mental health facilities, and the like, so that the entire health care community is capable of integration on the network. Remote computers 28 may be a personal computer, server, router, a network PC, a peer device or other common network node, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, joy stick, game pad, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

The method and system of the present invention receives medical test results and translates the results into plain language understandable by the patient. Although the method and system are described as being implemented in a WINDOWS operating system operating in conjunction with an Internet based system, one skilled in the art would recognize that the method and system can be implement in any system supporting the receipt and processing of medical result information.

As best seen in FIGS. 2A-2E, the present invention receives medical test result information and translates the results into plain language understandable by a patient with little medical knowledge. The types of medical tests capable of translation are numerous and include blood, urine and other tests related to bodily fluids, imaging tests such as x-rays, magnetic resonance imaging (MRI) tests and mammograms, sensory tests related to vision, hearing, and speech, and cognitive tests. First, the results of the test are inputted into the system. Preferably, the results are inputted at one of the remote computers 28. By way of example, the test results may either be input into the memory of the remote computer by a clinician or personnel associated with the clinician, or received directly from the output of a medical testing device. The test results could also be inputted directly into server 22. At step 200, the test results are received from one of the remote computers 28, preferably via the network and central server.

Figure 2A:
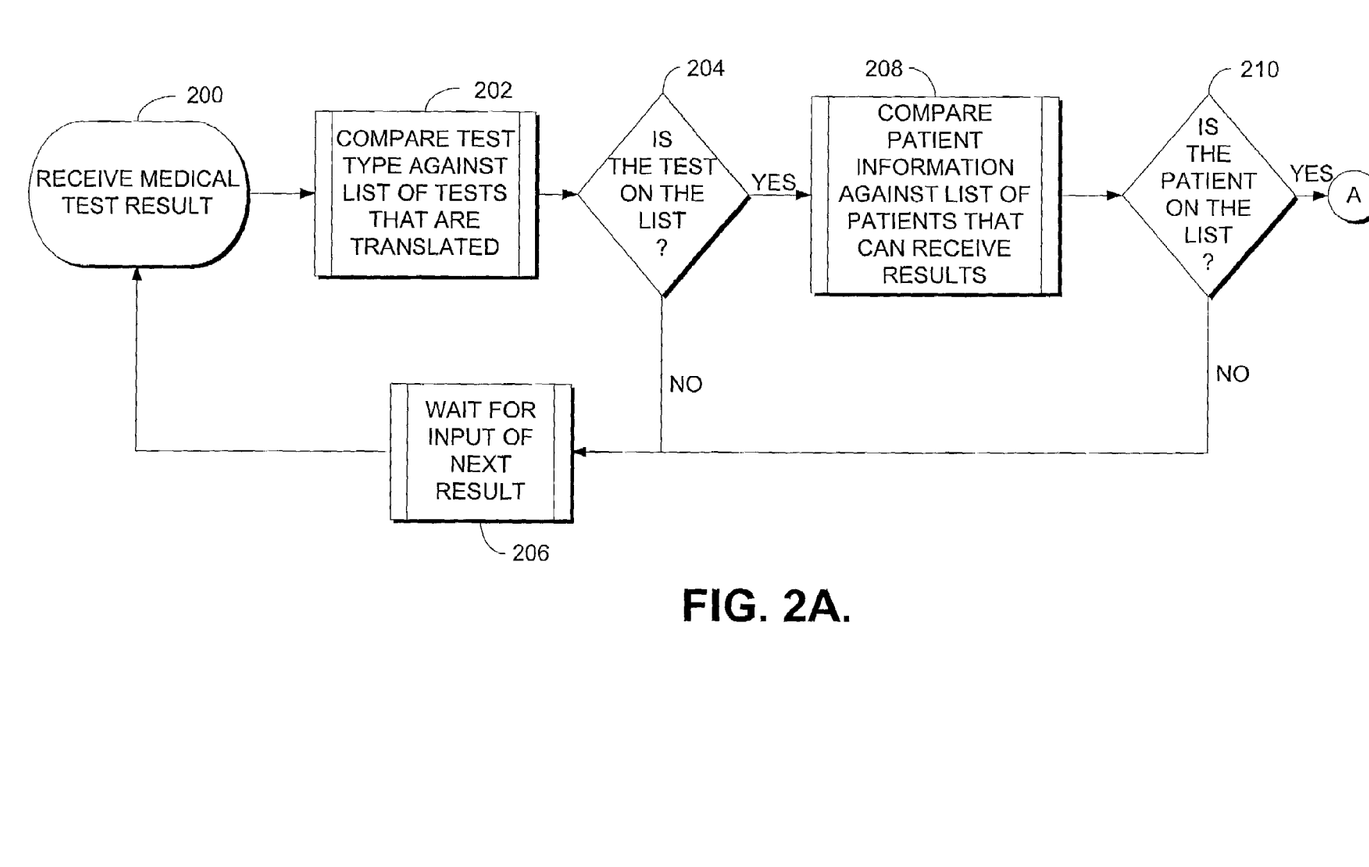
FIGS. 2A-2E are flow diagrams illustrating a preferred method for translating medical test results to plain language.

Preferably, the medical test results include an identification of the patient, an identification of the treating physician ordering the test, and the results themselves. The patient and treating physician may be identified by name, number or other type of identification. The results may be in various forms, including numerical values, textual observations, images of X-rays, scans and/or photographs, or any of a number of recognized forms and formats of medical test results.

Once the medical test result input is received, the system compares the test type to a list of tests that can be translated at step 202. The system has a stored list of medical tests that are capable of being translated by the system. This list is preferably stored in the database cluster 24. At step 204, the system determines if the test type is on the list stored in the system. If the test is not on the list, the system awaits the input and receipt of the next test result as indicated in step 206. However, if the test type for the particular medical test result is on the list, at step 208, the patient information component of the medical test result information is compared against a list of patients permitted to receive test results. The list of patients is preferably stored in the database cluster 24 and accessed by the control server 22. The list does not necessarily include all of the treating physician's patients. For example, minors, incompetents, and others that should not be allowed direct access to the test results are excluded from the stored list. However, the list may include members of the patient's family, guardians and other individuals that have legal access to the patient's test results.

Next, at step 210, the system determines if the patient is on the list. If the name or identification of the patient (or other authorized person) does not appear in the list, the system awaits the input and receipt of the next test result as indicated previously at step 206. If the patient is on the list at step 210, the system begins the process of translating the medical test result to a plain language interpretation as described in steps 212 through 234.

Figure 2B:
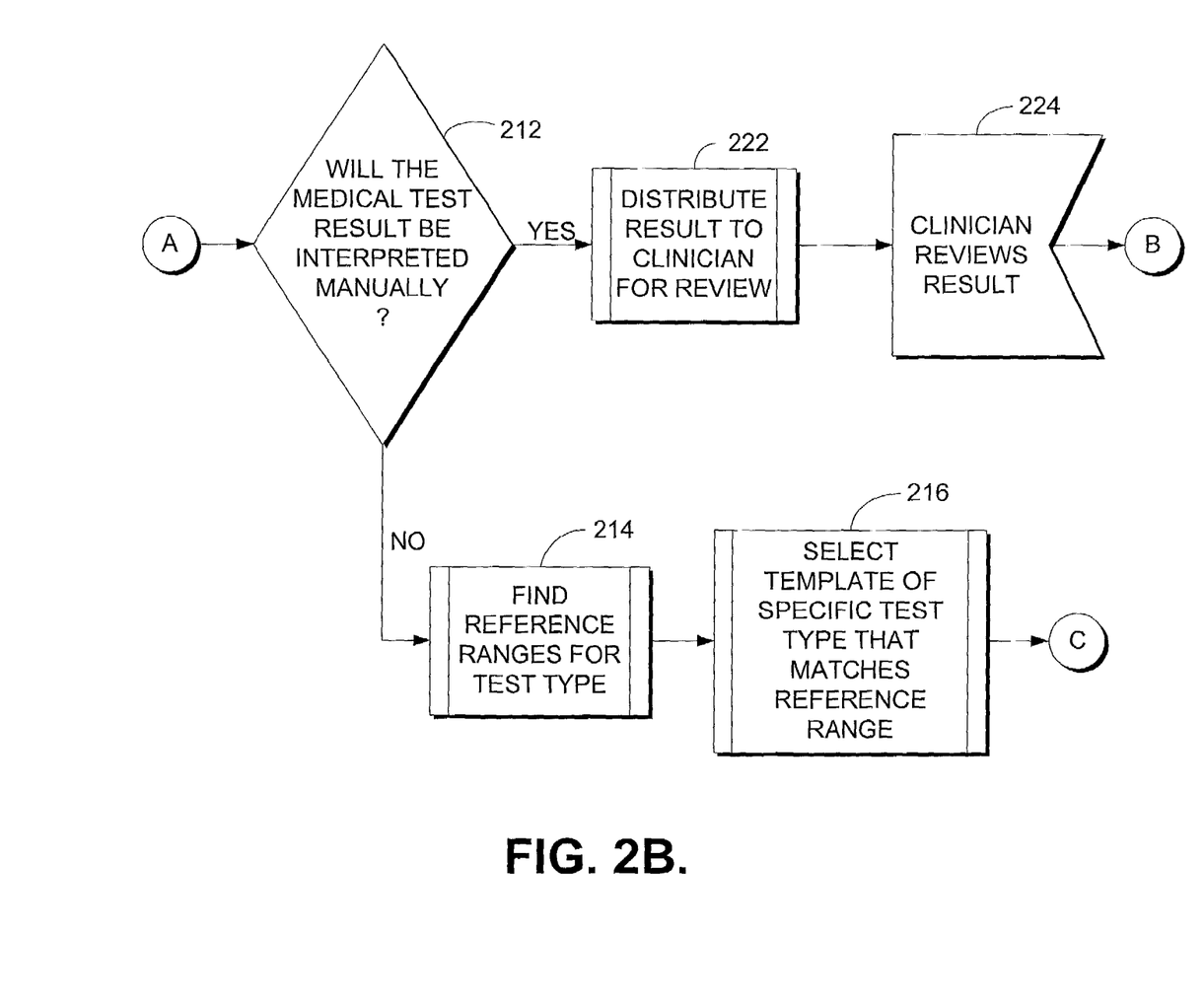

At step 212, the system determines if the medical test result will be interpreted by a clinician. If the result is not to be interpreted by a clinician, at step 214, the system finds reference ranges of test values associated with the type of test. A template or a set of templates are stored within the system for each particular test type. For those tests capable of interpretation by the system independently of a clinician, each template is associated with one or more specific test result values or a range of test result values for each particular test type. In step 216, the system selects the template that matches the reference value associated with test result or reference range within which the test result value falls. Then, at step 218, the system determines whether the selected template includes a tagged placeholder or placeholders for insertion of additional data. If one or more placeholders are present in the selected template, at step 220, additional data is embedded into the text of the template. The data may be numerical or textual result for the test, the date the test was performed, the name of the clinician performing the test, the name of the physician ordering the test, or any other type of predetermined text or value. If the template does not have tagged placeholders, step 220 is bypassed.

Figure 2C:
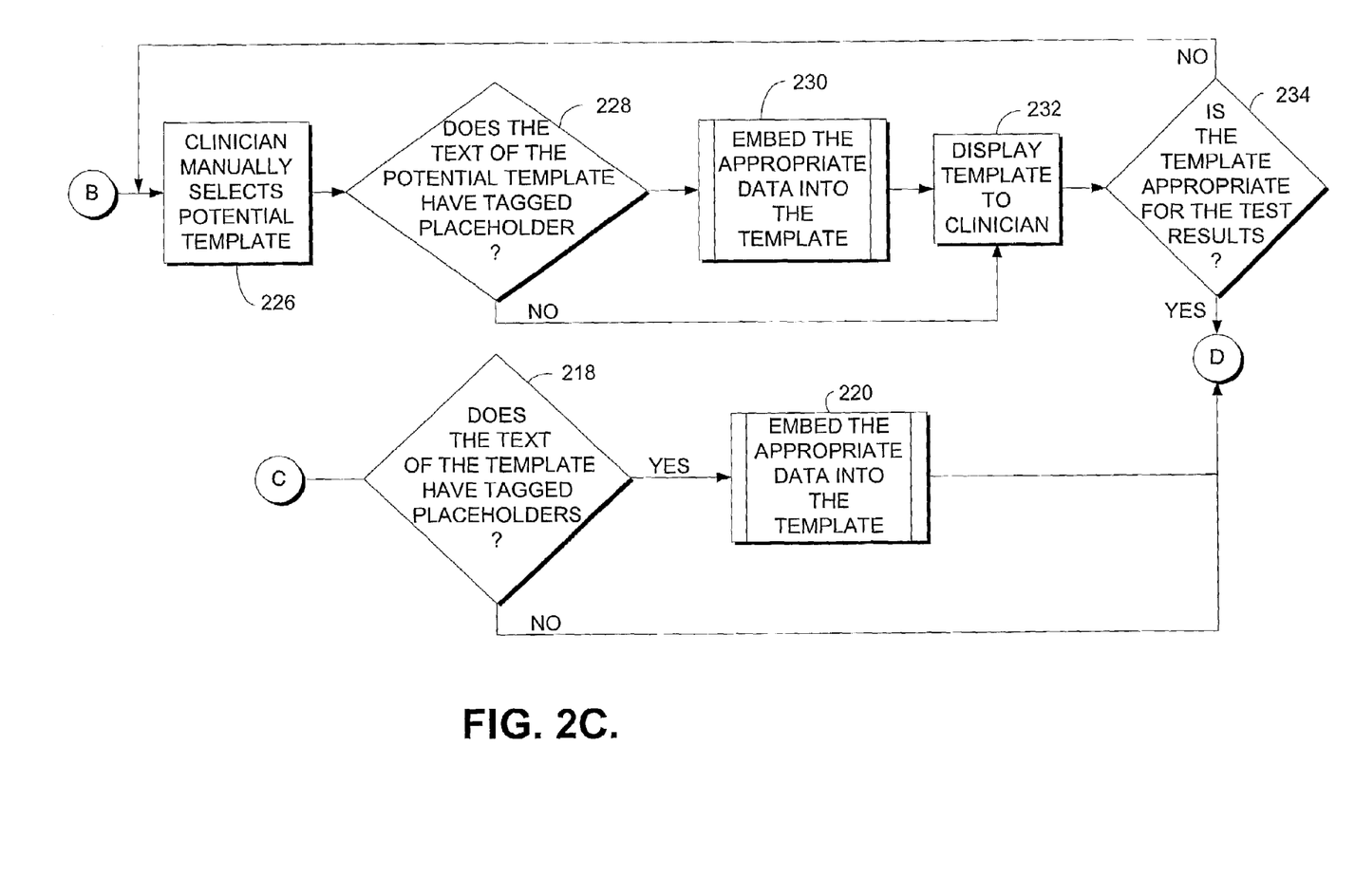

With reference back to step 212, if the result is to be interpreted manually by a clinician, the test result is distributed to the clinician at step 222. At step 224, the clinician reviews the results, and, at step 226, manually selects a potential template reflecting the clinician's interpretation of the results. For instance, a list of templates for the test type may be displayed, and one of the templates selected as the potential template corresponding the interpreted result. Once the clinician selects the potential template, the system determines if the potential template has tagged placeholders at step 228. If the template has placeholders, the appropriate data is embedded in the template at step 230. Once the information is embedded, the template is displayed to the clinician at step 232. If the text of the potential template does not contain tagged placeholders, step 230 is bypassed and the potential template is viewed by the clinician without any additional information. Once the template is viewed by the clinician at step 232, the clinician determines if the potential template is appropriate for the test results at step 234, and inputs the determination into the system. If the clinician determines that the potential template is not appropriate for the test results, then the system returns to step 226, and the manual selection steps are repeated.

Alternatively, instead of selecting from a list of potential templates, the clinician could manually select the results template from a set of potential templates in a variety of different ways understood by those of ordinary skill in the art. For instance, the first potential template of the set of potential templates could be viewed by the clinician automatically without any input from the clinician. If the text of the first template included a tagged placeholder, the appropriate data would be embedded prior to displaying the template. If the first template was deemed appropriate, the clinician could select the template as the results template. If the first template was not appropriate, the clinician could proceed to the next template in the set by indicating that the first template did not correspond to the test results. This process could be repeated until the appropriate template was identified by the clinician. In a variation of this alternative, each of a number of potential templates could be displayed simultaneous on a common display with any additional data embedded at the placeholders within the text of the templates. Then, the clinician could simply select the template corresponding to the test result.

In another alternative, the present invention contemplates manual selection of the appropriate potential template by the clinician without the steps of displaying the results template or determining if the potential template is appropriate. For instance, as more fully set forth below, if the clinician's interpretation indicated a positive or negative result, the clinician could select the appropriate potential template, and the system could identify any tagged placeholders, embed the additional data, and proceed directly to step 236 without displaying the results template to the clinician.

Figure 2D:
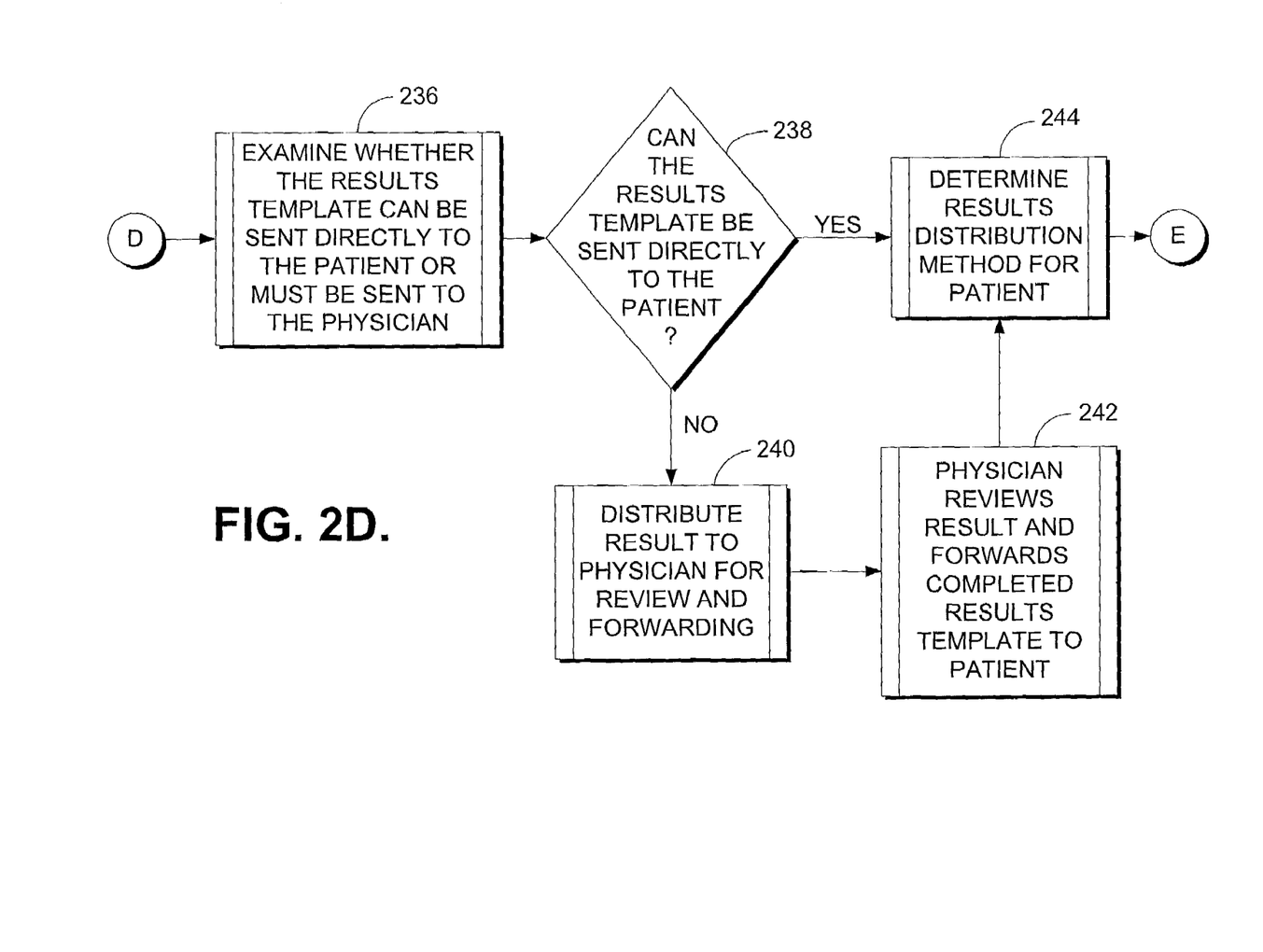

Once the results template is selected either automatically or manually, at step 236, the system determines whether the template can be sent directly to the patient or must be sent to the physician first. Specifically, at step 238, the system determines whether the result can be sent directly to the patient. If it cannot be sent directly to the patient, the system distributes the results to the physician for review and forwarding at step 240. At step 242, the physician reviews the results and forwards the completed results template to the patient.

In the preferred embodiment of the invention set forth above, a treating physician orders the test and a clinician performs the tests, and, in some instances, manually interprets the results. However, the system contemplates that a clinician other than the treating physician could order the test(s). Also, the test result could be manually interpreted by the treating physician rather than another clinician in the health care system. Notably, if the treating physician is the clinician making the manual selection at steps 226, 228, 230, 232 and 234, steps 240 and 242 are redundant and could be bypassed without departing from the scope of the invention.

Figure 2E:
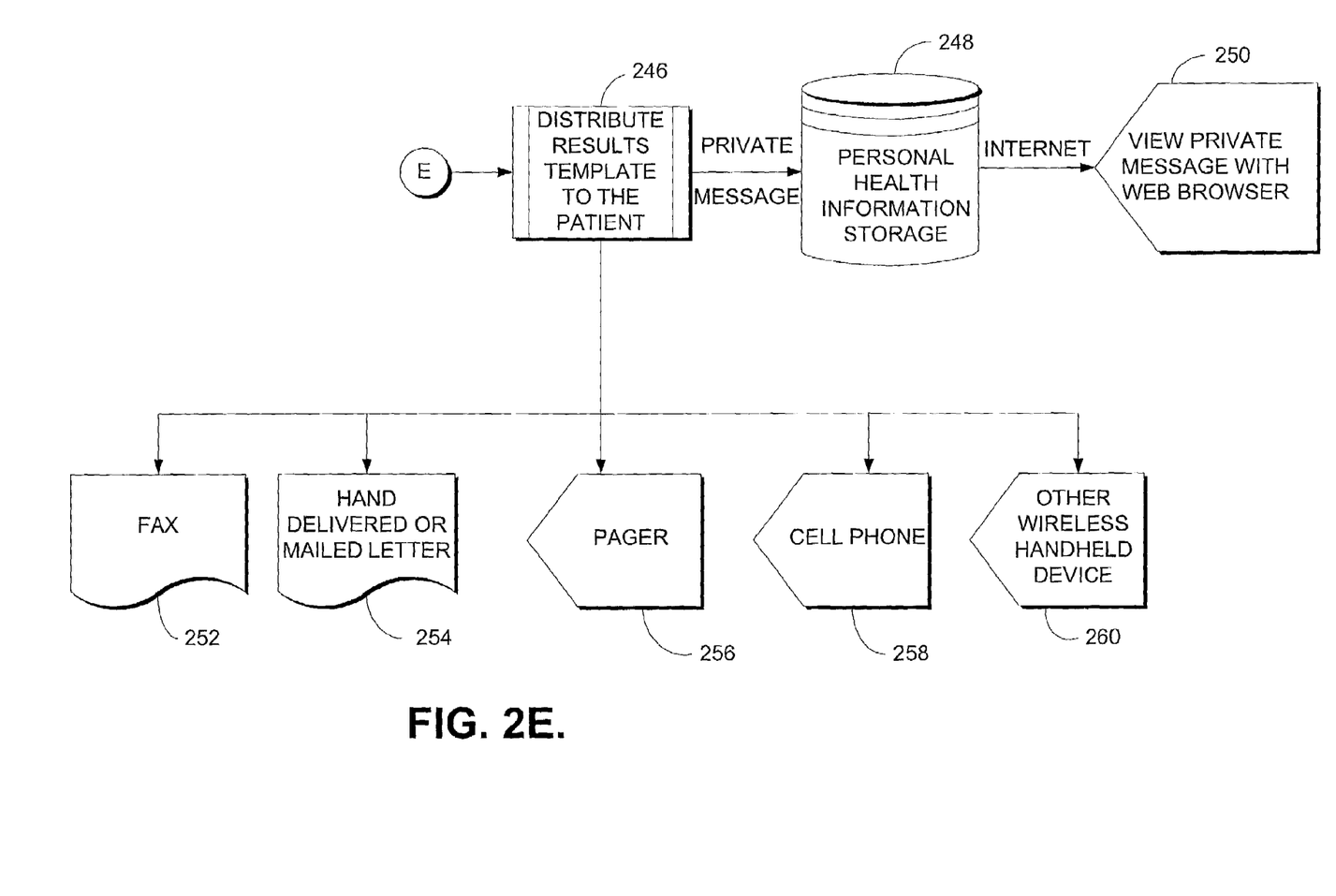

Whether the result can be sent directly to the patient or not, the system ultimately determines the results distribution method for the patient at step 244. Once the results distribution method is determined by the system, the results are distributed to the patient at step 246 as shown in FIG. 2E. Next, a private message is sent to the personal health information storage database at step 248. Preferably, the message is communicated to a network through the Internet at step 250 and viewable with a web browser. The results may also be distributed to the patient by any of a number of communications devices. For example, the results may be distributed by faxing the results at step 252, hand delivering or mailing a letter with the results at step 254, sending the results via a pager at step 256, sending the results as a voice message on a cellular phone as designated in step 258, or distributing the results to another wireless device such as personal digital assistant (PDA) at step 260.

In operation, an embodiment of the translation feature of the system is now described by way of example. When a patient visits the physician's office, a blood sample is taken. The physician sends the blood sample to a laboratory for a cholesterol test, and the lab determines the total cholesterol count of the patient. The laboratory technician inputs the medical test result information in a remote computer located in the laboratory. Specifically, the technician enters the patient's name, the physician's name and the results value at step 200. In this example, the test results include a value of 205 mg/dl. The test results are communicated from the remote computer to the control server via the network 26, preferably through a private network connection. Next, the system compares the cholesterol test type against the list of tests that are capable of translation at step 202. At step 204, the system determines that the cholesterol test is on the list of test types capable of translation. At step 208, the system determines if the patient identified in the test results can receive the results by comparing the patient information component of the medical test results to the list of patients stored in the system.

At step 210, the system determines that the patient is on the list and proceeds to determine if the result should be interpreted manually by a clinician at step 212. Since a cholesterol test is of the type that does not have to be interpreted by a clinician, the system finds reference ranges associated with cholesterol test results. For example, for a cholesterol test, the reference ranges may be associated with low, borderline low, normal, borderline high, and high cholesterol values. Specifically, for purposes of this example, a normal range of cholesterol results may be between 160 to 200 mg/dl and a borderline high range may encompass results between 201 mg/dl to 240 mg/dl. Once the reference ranges are found for the particular type of test, at step 216, the system selects the template for the reference range within which the test result value falls. In this example, for a cholesterol lab result of 205 mg/dl, falling within the range of values between 201 to 240 mg/dl, the predetermined "borderline high" template is selected.

Each of the templates includes information in plain language for the test results that fall within the reference range. Also, the template may contain a placeholder or placeholders for insertion of additional data for the particular test result. By way of this example, the template may have a first placeholder for the date on which the test was performed, and a second placeholder for inserting the numerical value of the patient's cholesterol level. By way of specific example, the template may read as follows:

"Your total cholesterol result on [first placeholder] is [second placeholder] mg/dl. Based on a normal range of 160 to 200 mg/dl, your result of [second placeholder] is considered borderline high. This may put you at increased risk for health problems such as heart disease and stroke. Therefore, you should speak with your doctor about ways to minimize your risk with changes in diet and exercise. Please read the attached documentation describing what cholesterol is, why it's important and how you can manage your own cholesterol."

Once the system determines that the text of the template has tagged placeholders at step 218, the date of the test and the test result value are embedded into the template at the appropriate placeholders at step 220 to generate the results template. Then, at step 236, the system examines whether the results template can be sent directly to the patient. For the cholesterol test, if the system determines that the result can be sent to the patient at step 238, the results may be distributed at step 244 without the review of the treating physician.

Alternatively, if the results template cannot be sent directly to the patient, the results are distributed to the physician for review and forwarding at step 240. Once the physician reviews the results at step 242, the results template is distributed in accordance with steps 244 and 246 and the physician's selection is recorded in the system. In this example, the distribution of results to the patient at 246 is made via a private message to the personal health information storage. Specifically, the results are incorporated in the patient's personal health record, and may be accessed via the Internet by the user at step 250.

The preceding example describes the selection of the results template by determining the template having a range encompassing the numerical test result value. Alternatively, as mentioned previously, each of the results templates may correspond to one or more specific test result value rather than a range. For instance, the identified set could comprise a first template specifically corresponding to a medical test result of "POSITIVE" and a second template specifically correspondence to a medical test result of "NEGATIVE." Likewise, the specific medical test result value could be input as a shorthand textual abbreviation or even a specific numerical value. It is also within the purview of the present invention to have some results templates of the identified set correspond to a range of values and other results templates within the set correspond to one or more specific value. For instance, one results template could correspond to a specific numerical test result value such as "0", or a textual result value of "INCONCLUSIVE," and each of the remainder of the results templates correspond to a range of numerical values.

In another alternative, the system could store a single results template for a medical test type. For instance, a single results template related to a test result of "NEGATIVE" could be stored, and identified by the system when the a medical test result of the relevant type was received. If the test result was negative, the single results template would be selected and output in accordance with the system. If the test was positive, the result could be distributed by a phone call, visit or other conventional method rather than via the system and method of the present invention.

In another example, mammogram results are interpreted via the system and method of the present invention. In this example, the patient has a mammogram performed. The results of the mammogram are stored in a remote computer at the physician's office and communicated to the control server 22 via a network 26. Again, after the information is received at step 200, the mammogram test is compared against the list of tests that are capable of being translated at step 202. If the mammogram test is on the list, at step 204, the patient information component of the medical test results is compared against a list of patients that can receive results. At step 210, if the patient is on the list, the next step is to determine whether the result will be interpreted by the physician at step 212.

Since a mammogram does not involve a specific value that falls within a range, the result is typically interpreted by a clinician. Accordingly, the results are distributed to a clinician for review at step 222, and the clinician reviews the test results and selects one of a number of potential templates related to a mammogram test at step 236, and the selection is recorded in the system. By way of example, the set may include templates for abnormal and normal results. If the abnormal result template is selected by the physician, the text may read as follows, with the placeholder indicated in brackets:

"Your mammogram performed on [date placeholder], has shown an abnormality and further tests are needed. It is very important that you call your physician for details of your report and to schedule the additional tests that may be necessary. A copy of your report has been forwarded to your physician.

Please keep in mind that good breast care involves a combination of three important steps.

1. Monthly breast self examinations.
2. Yearly physical examination by your physician.
3. Periodic mammograms according to your age and physician's recommendations.

For further reference, always remember to inform any new physician of the date and place of your last mammogram. Your original films will be kept as part of your permanent medical record at County Memorial Hospital."

Conversely, the normal template may read as follows:

"Your mammogram performed on Oct. 1, 2000 did not show any sign of cancer. A copy of your report has been forwarded to your physician.

Please remember that some cancers (about 8% to 10%) cannot be found by mammography alone, and that early detection requires a combination of monthly breast self-examinations, a yearly physical examination, and periodic mammograms. The American Cancer Society recommends the following time line for mammography examination.

| AGE | RECOMMENDATIONS |
| --- | --- |
| 35-40 | Baseline (first) mammogram |
| 40 and over | Yearly mammograms |

Please continue regular self-examination and report to your physician any changes that concern you, even before your next appointment. For future reference, always remember to inform any new physician or mammography facility of the date and place of your last mammogram. Your original films will be kept as part of your permanent medical record at County Memorial Hospital."

At steps 228 and 230, the placeholder is identified and the date is inserted into the template at the placeholder. Then, the results template with the date is preferably display to the clinician at step 232 and selected at step 234. Next, at step 236, it is determined whether the test can be sent directly to the patient or must be sent to a physician first. Again, if the tests must be sent to the physician for review and forwarding, steps 240 and 242 are performed by the system. If not, the system goes to step 244 to determine the distribution method for the patient. Finally, at step 246, the results may be distributed in any of a number of ways. For this example, the results could be distributed by a letter addressed to the patient as indicated at step 254.

Alternatively, a single results template associated with a normal test result may be stored for a particular test type such as the mammogram described above. If the interpretation of the clinician indicated a test result of normal, the clinician would select the template and the results template would be distributed in accordance with the present invention. If the interpretation indicated an abnormal result, the clinician would not select the template, and would communicate the results by conventional methods.

Although the invention has been described with reference to the preferred embodiment illustrated in the attached drawing figures, it is notes that substitutions may be made and equivalents employed herein without departing form the scope of the invention as recited in the claims.

The invention claimed is:

1. A method in a computer system for translating medical test results into plain language, comprising the steps of:
   receiving a medical test result for a type of medical test;
   prior to interpreting the medical test result to provide a plain language explanation for the medical test result, making a threshold determination whether the medical test result will initially be automatically interpreted by the computer system independent of clinician input or the medical test result will be interpreted using clinician input without an initial automatic interpretation by the computer system;
   if the medical test result will initially be automatically interpreted independent of clinician input, identifying at least one template associated with the type of medical test;
   selecting a template matching the medical test result; and
   outputting a plain language explanation based on the selected template.

2. The method of claim 1, wherein identifying at least one template associated with the type of medical test comprises identifying a set of a plurality of templates associated with the type of medical test.

3. The method as recited in claim 2, wherein each template of the identified set corresponds to a range of medical test result values.

4. The method as recited in claim 3, wherein the selecting step includes determining a template corresponding to the range encompassing the medical test result.

5. The method as recited in claim 2, wherein each template of the identified set corresponds to a medical test result value.

6. The method as recited in claim 5, wherein the selecting step includes determining a template corresponding to the medical test result value.

7. The method as recited in claim 1, further comprising:
   if the medical test result will be interpreted using clinician input, distributing the medical test result to the clinician without initially automatically interpreting the medical test result by the computer system, and wherein the selecting step includes receiving clinician input, the input matching the medical test result to a template.

8. The method as recited in claim 7, further comprising the step of recording the input of the clinician.

9. The method as recited in claim 1, further comprising the step of receiving patient information and comparing the patient information against a list of patients having authorization to receive the medical test result.

10. The method as recited in claim 1, wherein the selected template includes at least one placeholder.

11. The method as recited in claim 10, further comprising the step of inserting data into the selected template at the placeholder.

12. The method as recited in claim 11, wherein the data is a numerical value for the medical test result.

13. The method as recited in claim 1, further comprising the step of determining whether the selected template can be sent directly to a patient.

14. The method as recited in claim 1, wherein the outputting includes sending a message to a storage unit and adapting the selected template for viewing via a web browser.

15. The method as recited in claim 1, wherein the outputted plain language explanation is textual.

16. The method as recited in claim 1, wherein the outputted plain language explanation is audible.

17. The method as recited in claim 16, wherein the plain language explanation is delivered by an automated phone system.

18. The method as recited in claim 16, wherein the plain language explanation is delivered by a wireless device.

19. The method as recited in claim 1, further comprising the step of distributing the medical test result and the selected template to a physician for review prior to the step of outputting a plain language explanation based on the selected template.

20. A computer system for translating medical test results into plain language, comprising:
   a receiving component that receives a medical test result for a type of medical test for a patient;
   an identifying component that identifies at least one template associated with the type of medical test;
   a determining component that determines whether the medical test result is a normal test result appropriate for automated delivery to the patient by the computer system or an abnormal test result inappropriate for automated delivery to the patient by the computer system;
   a selecting component that selects a template matching the medical test result if the medical test result is determined to be a normal test result;
   an outputting component that outputs a plain language explanation based on the selected template if the medical test result is determined to be a normal test result and outputs an abnormal indication to a clinician for manual delivery of the medical test result to the patient if the medical test result is determined to be abnormal; and
   a distribution component that automatically distributes the plain language explanation to the patient if the medical test result is determined to be a normal test result.

21. The system as recited in claim 20, wherein the identifying component identifies a set of a plurality of templates associated with the type of medical test.

22. The system as recited in claim 21, wherein each template of the identified set corresponds to a range of medical test result values.

23. The system as recited in claim 22, wherein the selecting component includes a determining component that determines a template corresponding to the range encompassing the medical test result.

24. The system as recited in claim 21, wherein each template of the identified set corresponds to a medical test result value.

25. The system in claim 24, wherein the selecting component includes an identifying component that identifies the template corresponding to the medical test result value.

26. The system as recited in claim 20, further comprising:
   a medical test result distributing component for distributing the medical test result to a clinician if the medical test result will be interpreted using clinician input, and wherein the selecting component receives input from a clinician, the input matching the medical test result to a template.

27. The system as recited in claim 26, further comprising a recording component that records the input of the clinician.

28. The system as recited in claim 20, further comprising a receiving component that receives patient information and a comparing component that compares the patient information against a list of patients having authorization to receive the medical test result.

29. The system as recited in claim 20, wherein the selected template includes at least one placeholder.

30. The system as recited in claim 29, further comprising an inserting component that inserts data into the selected template at the placeholder.

31. The system as recited in claim 30, wherein the data is a numerical value for the medical test result.

32. The system as recited in claim 20, wherein the distribution component includes a sending component that sends a message to a storage unit and an adapting component that adapts the selected template to a format viewable via a web browser.

33. The system as recited in claim 20, wherein the outputted plain language explanation is textual.

34. The system as recited in claim 20, wherein the outputted plain language explanation is audible.

35. The system as recited in claim 34, wherein the distribution component comprises an automated phone system that delivers the plain language explanation.

36. The system as recited in claim 20, wherein the distribution component comprises a wireless device that delivers the plain language explanation.

37. The system as recited in claim 20, further comprising a distributing component for distributing the medical test result and the selected template to a physician for review before the outputting component outputs a plain language explanation based on the selected template.

38. A computer-readable medium storing instructions for controlling a computer system to translate medical test results into plain language, by:
   receiving a medical test result for a type of medical test;
   determining the type of medical test for the medical test result is a type that may be interpreted using the computer system by comparing the type of medical test for the medical test result to a list of medical test types capable of being interpreted using the computer system;
   determining that a patient associated with the medical test result is permitted direct access to medical test results by comparing patient information associated with the medical test result that identifies the patient against a list of patients permitted to receive medical test results;
   prior to interpreting the medical test result to provide a plain language explanation for the medical test result, making a threshold determination whether the medical test result will initially be automatically interpreted by the computer system independent of clinician input or the medical test result will be interpreted using clinician input without an initial automatic interpretation by the computer system;
   if the medical test result will initially be automatically interpreted independent of clinician input:
      automatically identifying at least one template associated with the type of medical test,
      automatically selecting a template matching the medical test result, and
      outputting a plain language explanation for the medical test result based on the selected template; and
   if the medical test result will be interpreted using clinician input without an initial automatic interpretation by the computer system;
      distributing the medical test result to the clinician,
      receiving clinician input matching the medical test result to a template, and
      outputting a plain language explanation based on the selected template.

39. The computer-readable medium as recited in claim 38, wherein identifying at least one template associated with the type of medical test comprises identifying a set of a plurality of templates associated with the type of medical test.

40. The computer-readable medium as recited in claim 39, wherein each template of the identified set corresponds to a range of medical test result values.

41. The computer-readable medium as recited in claim 40, wherein the selecting step includes determining a template corresponding to the range encompassing the medical test result.

42. The computer-readable medium as recited in claim 39, wherein each template of the identified set corresponds to a medical test value.

43. The computer-readable medium of claim 42, wherein the selecting step includes identifying the template corresponding to the medical test result value.

44. The computer-readable medium as recited in claim 38, further comprising the step of recording the input of the clinician.

45. The computer-readable medium as recited in claim 38, wherein the selected template includes at least one placeholder.

46. The computer-readable medium as recited in claim 45, further comprising the step of inserting data into the selected template at the placeholder.

47. The computer-readable medium as recited in claim 46, wherein the data is a numerical value for the medical test result.

48. The computer-readable medium as recited in claim 38, further comprising the step of determining whether the selected template can be sent directly to a patient.

49. The computer-readable medium as recited in claim 38, wherein the outputting includes sending a message to a storage unit and adapting the selected template for viewing via a web browser.

50. The computer-readable medium as recited in claim 38, wherein the outputted plain language explanation is textual.

51. The computer-readable medium as recited in claim 38, wherein the outputted plain language explanation is audible.

52. The computer-readable medium as recited in claim 51, wherein the plain language explanation is delivered by an automated phone system.

53. The computer-readable medium as recited in claim 51, wherein the plain language explanation is delivered by a wireless device.

54. The computer-readable medium as recited in claim 38, wherein if the medical test result will initially be automatically interpreted independent of clinician input, the method further comprises the step of distributing the medical test result and the selected template to a physician for review prior to the step of outputting a plain language explanation based on the selected template.

* * * * *